(12) United States Patent
Grant et al.

(10) Patent No.: US 8,272,253 B2
(45) Date of Patent: Sep. 25, 2012

(54) PARTICLE CONCENTRATION MEASUREMENT TECHNOLOGY

(75) Inventors: Donald C. Grant, Excelsior, MN (US);
Mark R. Litchy, Plymouth, MN (US);
David Blackford, North Oaks, MN (US)

(73) Assignee: CT Associates, Inc., Eden Prairie, MN (US)

( * ) Notice: Subject to any disclaimer, the term of this patent is extended or adjusted under 35 U.S.C. 154(b) by 665 days.

(21) Appl. No.: 12/357,088

(22) Filed: Jan. 21, 2009

(65) Prior Publication Data

US 2009/0183554 A1 Jul. 23, 2009

Related U.S. Application Data

(60) Provisional application No. 61/011,901, filed on Jan. 22, 2008.

(51) Int. Cl.
*G01N 15/06* (2006.01)
(52) U.S. Cl. .................................................. 73/61.72
(58) Field of Classification Search ................ 73/61.71, 73/61.72
See application file for complete search history.

(56) References Cited

U.S. PATENT DOCUMENTS

| 4,761,074 | A | * | 8/1988 | Kohsaka et al. | 356/37 |
| 4,794,086 | A | * | 12/1988 | Kasper et al. | 436/36 |
| 5,076,097 | A | * | 12/1991 | Zarrin et al. | 73/61.72 |
| 5,098,657 | A | * | 3/1992 | Blackford et al. | 422/73 |
| 5,247,842 | A | * | 9/1993 | Kaufman et al. | 73/865.5 |
| 7,777,868 | B2 | * | 8/2010 | Blackford et al. | 356/37 |

* cited by examiner

*Primary Examiner* — Daniel Larkin
(74) *Attorney, Agent, or Firm* — Skinner and Associates

(57) ABSTRACT

A method and apparatus for measuring particle concentration and size distribution of particles in liquids. The method involve separating dissolved and particulate residues in liquids for determination of the size and concentration of the particulate species. The method includes the steps of forming an aerosol from the liquid sample to be analyzed, evaporating the droplets in the aerosol to dryness, and detecting the particles. An apparatus for separating dissolved and particulate residues in liquids for determination of the size and concentration of the particulate species is also disclosed. The apparatus includes a droplet former, a dryer communicatively connected to the droplet former, and a detector communicatively connected to the evaporator for detecting particles.

10 Claims, 17 Drawing Sheets

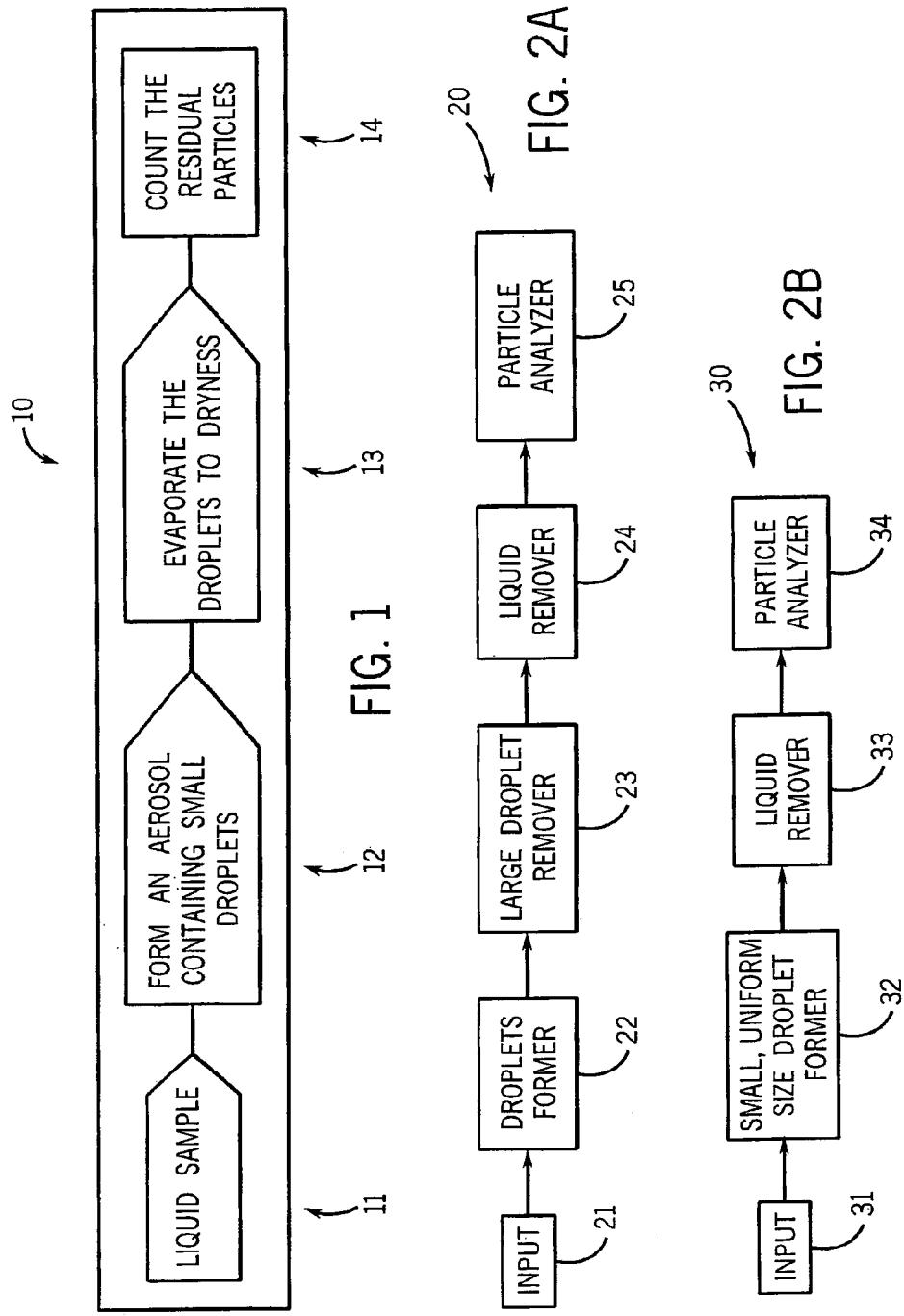

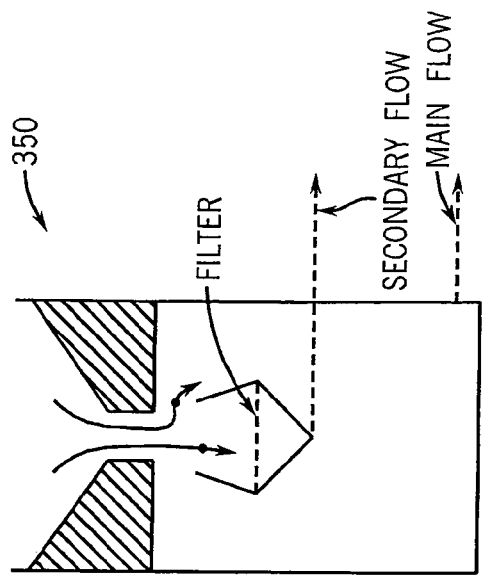
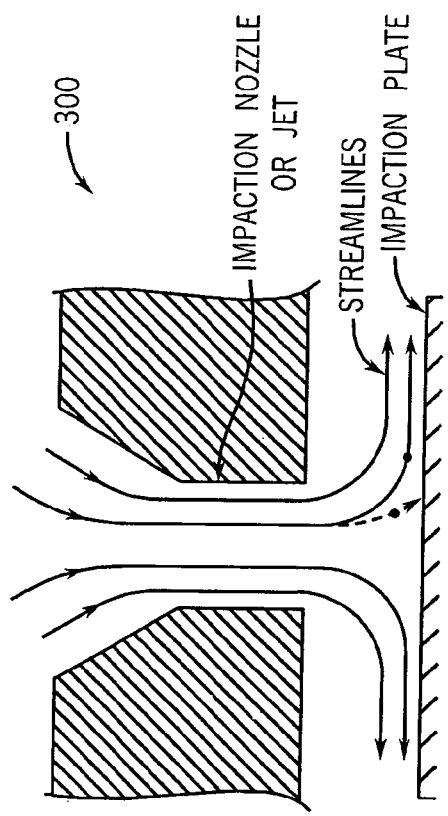
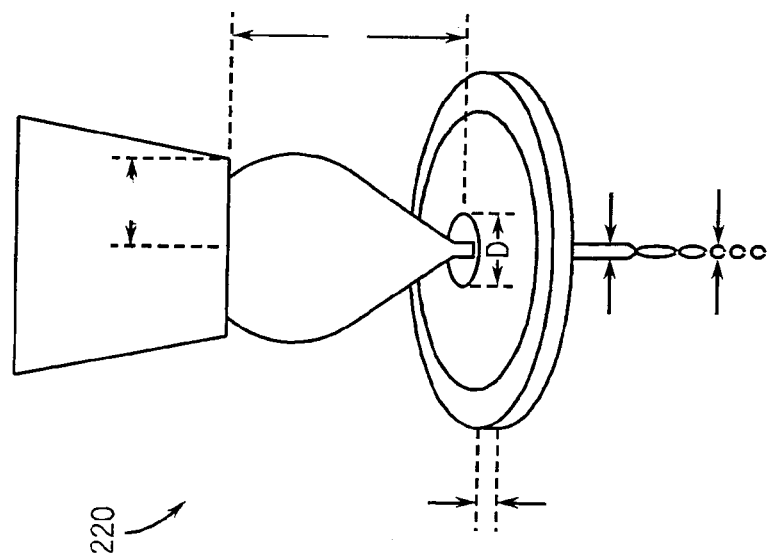

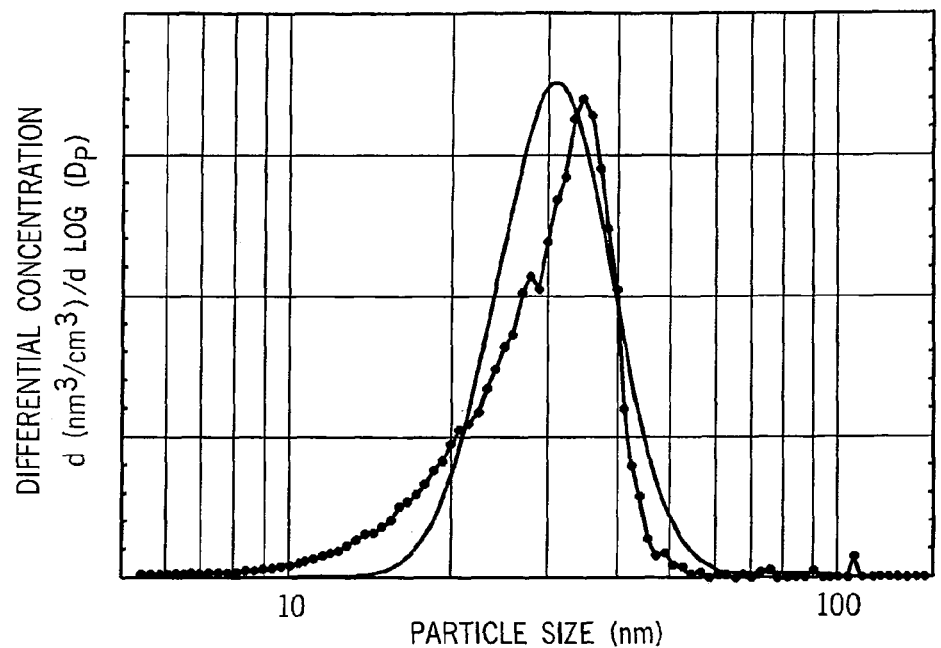
FIG. 16 •— SMPS —— NICOMP 380ZLS
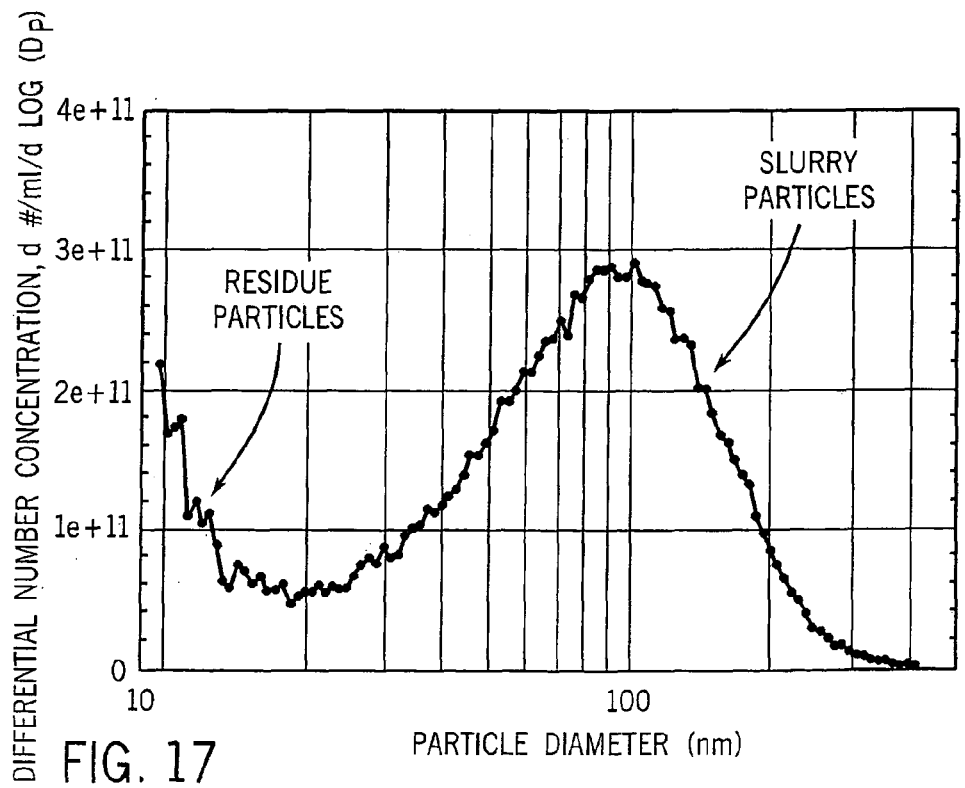
FIG. 17

PARTICLE CONCENTRATION MEASUREMENT TECHNOLOGY

CROSS-REFERENCE TO RELATED APPLICATIONS, IF ANY

This application claims the benefit under 35 U.S.C. §119(e) of U.S. Provisional Patent Application Ser. No. 61/011,901, filed Jan. 22, 2008, which is hereby incorporated by reference.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND

1. Field

The present invention relates, generally, to analysis methods and apparatus for use with compositions of matter. More particularly, the invention relates to a method and apparatus for measuring the size and concentration of small particles in high purity liquids and colloidal suspensions. Most particularly, the invention relates to an apparatus and method for separating dissolved and particulate residues in a liquid to determine the size distribution and concentration of the particulate species (i.e. particles). The technology is useful, for example, for accurate measurement of low concentrations of very small (sub 50 nm) particles in high purity liquids, the measurement of particle retention by filters, and measurement of particle size distributions in colloidal suspensions. The invention is suitable for use in the semiconductor device manufacturing industry, the ink manufacturing industry, and in other fields.

2. Background Information

The present invention has utility in measurement of the concentration of small, for example, sub 50 nm., particles in high purity liquids. Small particles are a major problem for the semiconductor device manufacturing industry. Particles smaller than 50 nm can significantly reduce manufacturing yield of present day semiconductor devices. The ability to measure concentrations, especially low concentrations, of these particles is highly desired. Insofar as is known, there is no technology to meet this need.

The present invention also has utility in measurement of particle retention by filters, particularly those with pore sizes smaller than about 50 nm. Microporous membrane filters are often used to reduce particle levels in liquids for semiconductor device manufacturing. The ability of filters of this type to remove particles from the liquids is usually determined by challenging the filters with particles and measuring what comes through. Instruments capable of measuring particles of these sizes are not believed to be available.

The invention further has utility in measurement of Particle Size Distributions (PSD) in colloidal suspensions. There are numerous applications in which the size distribution of particles in colloidal suspensions is important in determining the efficacy of the suspension. Examples include slurries used in chemical mechanical planarization (CMP) of silicon wafers, as well as wafers composed of other materials, during semiconductor chip manufacturing and pigment-based inks. The PSD of CMP slurries determines the planarization rate, surface smoothness and scratch density on the wafer surface following the CMP process. All of these are important in determining the finished semiconductor device yield and performance. The size distribution of pigment inks is important in determining color development.

Historically, the first application mentioned above, measurement of concentrations of small particles (particularly those less than 50 nm in size) in high purity liquids has been addressed using single particle optical particle counters (OPCs). These instruments size and count individual particles as they pass through a laser beam. They have met the need of the semiconductor industry until recently, although they have typically been believed to have been a half step behind in development. Approximately twenty years ago the industry needed to detect roughly 500 nm particles; now they desire to measure 20-30 nm particles. The problem is that below about 300 nm the amount of light scattered by a particle is proportional to the $6^{th}$ power of the diameter ($D_P^6$). Therefore, an instrument to measure 30 nm particles needs to be 1,000,000 times more sensitive than one that measures 300 nm particles. A leading company in making these counters has been Particle Measuring Systems. Their highest sensitivity in water is claimed to be 50 nm, but it is believed to be closer to 60-70 nm. Claimed sensitivity in chemicals is 65 nm. Particle Measurement Systems had a counter with a claimed sesnsitivity of 30 nm counter on the market at one time, but it is no longer available. Other companies that make counters of this type are RION, Horiba, Particle Sizing Systems, and Hach Ultra.

Very small particles (typically smaller than 10 nm) in liquids have also been analyzed using a combination of electrospray and mass spectroscopy. Electrospray is used to generate small droplets by subjecting the liquid to a high electric field. The liquid must be moderately conductive and the droplets become highly charged during formation. High purity liquids typically have low conductivity making the formation of small droplets difficult. Also, the high charge on the particles can result in particle agglomeration and may cause other changes in particle properties. The agglomeration issue can be addressed by exposing the aerosol to ionizing radiation.

The second application, measurement of particle retention by filters with small pore sizes, has also been addressed using OPCs, again limited to 50 nm. Other techniques have also been used such as turbidimitry. However, these techniques can only be used at very high particle concentrations, concentrations well above those seen in high purity applications. And, filter performance at these high concentrations is not representative of performance at lower concentrations.

Filter performance has also been measured using nonvolatile residue monitors (NVRM or NRM). These instruments work by forming an aerosol of the particle-laden liquid, evaporating the liquid in the aerosol and measuring the number of particles in the aerosol. The problem with this method is that any dissolved material in the liquid forms a particle when the liquid is evaporated. Hence, the instrument measures both dissolved and particulate residue. And the residue particles interfere with the particulate particle measurement.

The third application, measurement of particle size distributions in colloidal suspensions, has typically been addressed using either dynamic light scattering (DLS) or centrifugal sedimentation. Both of these methods only measure relative PSDs. They cannot determine concentrations.

For these and other reasons, a need exists for the present invention.

All US patents and patent applications, and all other published documents mentioned anywhere in this application are hereby incorporated by reference in their entirety.

BRIEF SUMMARY

The present invention provides a method and apparatus for measuring (a) the concentrations of small particles, on the order of 50 nm or smaller, and (b) the size distributions of such particles, in liquids, which method and apparatus are practical, reliable, accurate and efficient, and which are believed to fulfill a need and to constitute an improvement over the background technology.

In a basic embodiment, the method of the present invention includes the steps of, providing a specimen to be tested, isolating small, uniformly sized droplets from the specimen, evaporating the droplets to dryness, and counting and sizing the particles that were originally (initially) in the liquid. Thereby, particle concentration and PSD may be determined. The method is especially effective for measuring low concentrations of very small particles, particularly those less than 50 nm in size.

In one aspect of the present invention, an apparatus includes a nebulizer/impactor and a condensation particle counter (CPC). The nebulizer/impactor has means to form or isolate small, uniformly sized droplets. The CPC accurately counts particles present after the small, uniformly sized droplets are dried. This embodiment is believed to be best suited for high purity liquid to measure particle concentration above a defined threshold, but without PSD measurement, a threshold particle counter (TPC).

In another aspect, the apparatus includes a nebulizer/impactor and a scanning mobility particle sizers (SMPS), which performs both particle counting and sizing. This embodiment is believed to be best suited for determining PSD in addition to particle concentration.

In a further aspect, a nebulizer/impactor combination is provided for generating an aerosol composed of multiple droplets of a liquid. The nebulizer/impactor includes a housing forming a mixing chamber having (i) a liquid entrance for receiving a sample liquid into the chamber, (ii) a primary orifice having a first diameter for receiving a pressurized gas into the chamber for merger with the sample liquid to generate an aerosol composed of multiple droplets of the sample liquid suspended in the gas, and (iii) a secondary orifice having a secondary diameter for conducting the aerosol out of the chamber. The second orifice is less than a major dimension of the mixing chamber taken in a direction substantially perpendicular to an axis of the secondary orifice, so as to restrict flow out of the mixing chamber to generate a back pressure in opposition to entry of the sample liquid and the pressurized gas into the chamber.

In contrast to other nebulizers in which the chamber exit is simply open to the downstream components with a diameter equal to that of the chamber, the exit orifice in the nebulizer in D has a diameter less than that of the chamber, more preferably less than half the diameter chamber. The diameter reduction provides a constriction that produces a higher kinetic energy mixing of the gas and liquid in the merger zone. As a result, the nebulizer generates smaller droplets. The secondary orifice also helps direct the aerosol toward the impactor surface raising the impactor efficiency.

Another factor reducing the droplet size produced by the atomizer/impactor is close axial positioning of an impactor just downstream of the secondary orifice. The more closely spaced impactor removes a greater proportion of the larger droplets.

In a preferred version of nebulizer/impactor, the impactor axial spacing from the secondary orifice is adjustable through movement of the impactor. For example, a threaded mounting of the impactor to the nebulizer frame allows axial position adjustment by turning the impactor about its longitudinal axis. The average size of the droplets in the aerosol leaving the nebulizer can be increased or decreased by respectively enlarging or reducing the axial spacing between the secondary orifice and the impactor. The average size can also be decreased and the uniformity increased by making the shape of the housing containing the secondary orifice conformal to the impactor shape.

The droplet size produced by atomizer/impactor also can be adjusted by changing or selecting the secondary orifice. Reducing the diameter of the secondary orifice is believed to increase back pressure and reduce droplet size. It has been found useful to provide a secondary orifice with a diameter larger than that of the primary orifice. The ratio of the secondary orifice diameter to the primary orifice diameter can range from slightly above one, to about two in versions that incorporate a secondary orifice.

The aspects, features, advantages, benefits and objects of the invention will become clear to those skilled in the art by reference to the following description, claims and drawings.

BRIEF DESCRIPTION OF THE SEVERAL VIEWS OF THE DRAWING

The present invention, and the manner and process of making and using it, will be better understood by those skilled in the art by reference to the following drawings.

FIG. 1 is a flow diagram of one embodiment of the method of the present invention.

FIG. 2A is a diagram illustrating an embodiment of the apparatus of the present invention.

FIG. 2B is a diagram illustrating an alternative embodiment of the apparatus of the invention.

FIGS. 3A-C illustrate pneumatic, concentric and flow focusing embodiments of a nebulizer component of the apparatus of the invention.

FIG. 4 is a cross sectional view of an embodiment of a plate impactor component which is used in an embodiment of the apparatus of the invention.

FIG. 5 is a cross sectional view of an embodiment of a virtual impactor which is used in another embodiment of the apparatus of the invention.

FIG. 16 is a graph of differential concentration versus particle size, which shows the ability to size 30 nm particle PSL.

FIG. 17 is a graph of CMP slurry PSD measured using a combination D apparatus with an SMPS detector.

DETAILED DESCRIPTION

The present invention provides a method and apparatus for determining the size distribution and concentration of particles in a liquid.

A. Methods of the Invention.

The method involves (a) forming droplets, for example via aerosolization, from a liquid sample to be analyzed, (b) isolating small droplets from the droplets, for example less than 10 um in size, (c) drying the droplets to remove the liquid, for example via evaporation, and (d) counting the residual particles.

Importantly, the aerosol droplets isolated are small and uniformly sized, less than 10 um and preferably a median size less than 1 um. The droplets must be small and uniformly sized because any dissolved material in the droplet will form a "residue" particle as a result of drying. If the residue particle is large enough it will be detected by the analyzer and interfere with the measurement of true, non-dissolved, particles.

The size of a residue particle resulting from evaporation of a liquid droplet can be determined from the concentration of the non-volatile residue in the droplet using equation 1 where $d_s$ is the size of the final residue particle, $d_d$ is the size of the droplet diameter and $F_v$ is the volume fraction of non-volatile residue in the droplet:

$$d_s=d_d(F_v)^{1/3} \quad (1)$$

If the density of the non-volatile residue in the droplet is the same as the liquid (1.0 g/cm$^3$ in the case of water), then $F_v$ is simply the weight concentration of non-volatile residue (C). If the water has a non-volatile concentration of 1 ppb with a density of 1.0, equation 1 above can be used to calculate the minimum droplet size that will yield a 25 nm particle, as follows:

$$d_d=d_s(C)^{-1/3}=25\text{ nm}(10^{-9})^{-1/3}=25\text{ nm}(1000)=25\ \mu\text{m}$$

Hence, the residue in droplets smaller than 25 μm will not be detected by a 25 nm CPC, if the CPC has a very sharp size cutoff.

The required small, uniformly sized droplets required by the present invention may be generated by firstly making droplets of diverse sizes and secondly removing large droplets. Alternatively, the desired droplets may be made in a single step. An example of the former embodiment of the method is implemented by generating droplets by a compressed air nebulizer or an ultrasonic nebulizer and then removing large droplets by directing them to an impaction surface such as a plate impactor or a virtual impactor. An example of generating small, uniform droplets directly is by way of a vibrating orifice aerosol generator. After the droplets are formed, liquid in the droplets is removed before the droplets collide or coalesce. Liquid removal may be accomplished by heating to dry via dilution air, heated air, or heating the liquid. It may also be accomplished by evaporation. And after drying to isolate the particles, the particles are counted and/or sized by OPC, CPC, SMPS or other instruments.

Thus, referring to FIG. 1, a flow chart of a basic embodiment of the method 10 of the invention involves the steps of, providing 11 a liquid sample, forming 12 very small, uniformly sized droplets, via an aerosol, from the liquid sample to be analyzed, drying 13, via evaporating, the droplets in the aerosol, and counting 14 the residual particles. Variants of this embodiment of the method are discussed above.

B. Apparatus of the Invention.

Referring to FIG. 2A, one embodiment of the apparatus 20 of the present invention comprises means 22 for forming droplets of diverse sizes connected to a sample input 21. Means 23 for removing large droplets is communicatively connected to the means 22 for forming droplets. An example of droplet former 22 is a compressed air nebulizer, an ultrasonic nebulizer, or a flow-focusing nebulizer, examples of which are shown in FIGS. 3A-3C. An example of means 23 for isolating small uniformly sized droplets is a plate impactor or a virtual impactor (examples of which are shown in FIGS. 4 and 5) having an impaction surface at which an aerosol stream output by the nebulizer 22 is directed and which removes large droplets. After the desired droplets are formed, liquid in the droplets is removed before the droplets collide or coalesce by liquid removal means 24. Examples of such means include a stream of dilution air, heated air, or a liquid heater. Drying may also be accomplished by a fast evaporator. A particle analyzer 25 is communicatively connected to the liquid remover 24. Examples of such an analyzer for counting and/or sizing includes an OPC, CPC, SMPS or other instrument or combination of instruments. Exemplary nebulizers, impactors and analyzers are described in detail below.

Referring to FIG. 2B, another embodiment of the apparatus 30 of the present invention comprises means 32 for making droplets of a small and uniform size connected to a sample input 31. An example of such means is a vibrating orifice aerosol generator, an example of which is described in detail below. After the desired droplets are formed, liquid in the droplets is removed before the droplets collide or coalesce by liquid removal means 33. Examples of such means include a stream of dilution air, heated air, or a liquid heater. Drying may also be accomplished by a fast evaporator. A particle analyzer 34 is communicatively connected to the liquid remover 33. Examples of such analyzer for counting and/or sizing includes an OPC, CPC, SMPS or other instrument or combination of instruments.

Testing of threshold particle counting of embodiments of the apparatus of the invention may be performed using the system 100 shown in FIG. 2C. In this system 100, particles of various types and sizes, for example a high purity liquid or a colloidal suspension, are injected into a flowing stream of UPW (input 110). Concentrations of the injected particles are measured using an HSLIS-M50 optical particle counter (OPC) 120 (of Particle Measuring Systems). A portion of the water is sent through a TPC combination nebulizer/impactor 130. The resulting aerosol is analyzed using three detector embodiments:

A 20 nm CPC 140

An SMPS 150, for example capable of measuring aerosol particle size distributions from 5 to 1000 nm.

A dew point sensor 160

The dew point sensor 160 is preferably used to measure the water vapor content of the gas containing the nebulized liquid to determine the instrument inspection volume. Under present optimum conditions, the instrument inspection volume is as large as practicable, preferably approximately 50-10,000 μlit/min [>100 μlit/min].

Processing may be performed with monodisperse polystyrene latex (PSL) particles of various sizes, polydisperse PSL, monodisperse silica particles or other particle types. For example, measurements may be made with 30 nm PSL, polydisperse PSL and 22 nm silica. The size distribution of the monodisperse particles tested can also be measured using a NICOMP 380ZLS (of Particle Sizing Systems). This instrument measures size distributions via dynamic light scattering (DLS)—a commonly used technique for measuring the size of small colloidal particles and the technique used by Duke Scientific (PSL bead supplier) to measure sub-50 nm PSL.

Figure 2C:
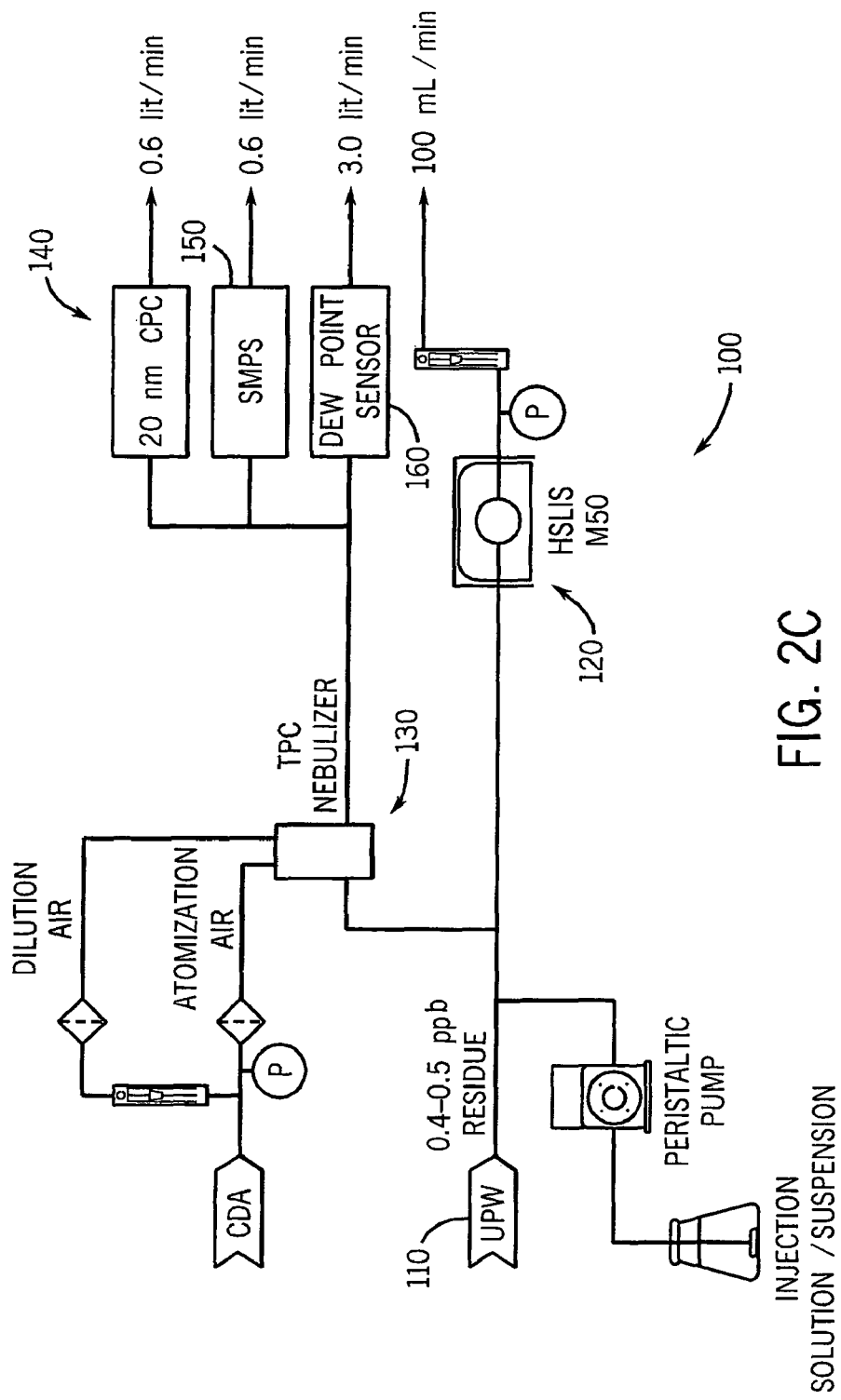
FIG. 2C illustrates an embodiment of an apparatus for testing or characterizing optimized threshold particle counting.
Figure 2D:
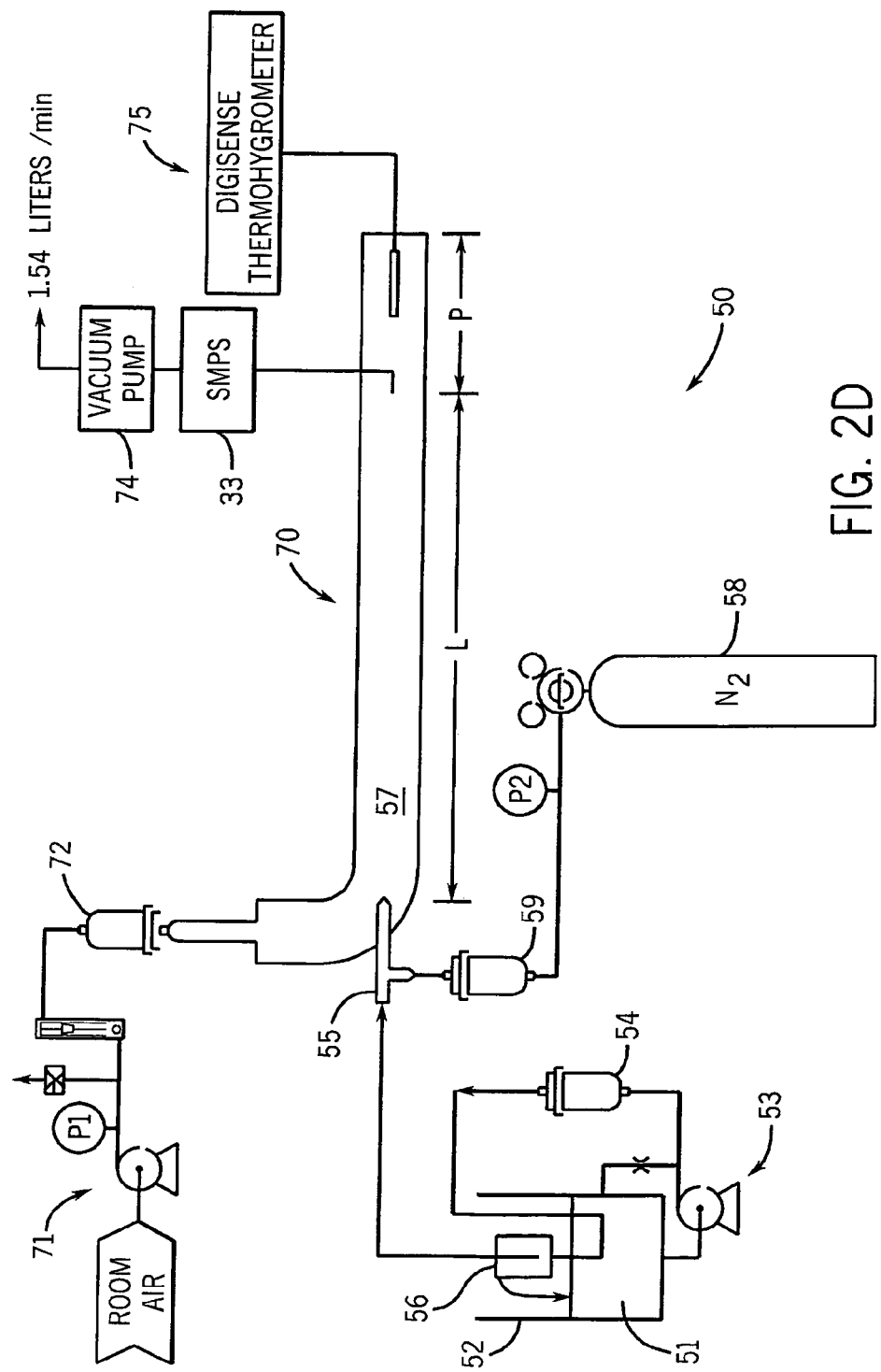
FIG. 2D illustrates a system for measuring droplet size distributions produced by droplet formers.

An apparatus for measuring the size distribution of droplets formed by various droplet forming methods is shown in FIG. 2D. A test solution 51 is input to a vessel 52. Solution 51 is output via a gear pump 53 through a filter 54 and into a small overflow vessel 56. Most of the liquid input to vessel 56 returns to vessel 52. A small portion of the liquid is sent to droplet former 55. Droplet former 55 forms an aerosol 57 containing small droplets. The nebulizer 55 is connected to a pressurized gas source 58, preferably compressed air or $N_2$. The gas is filtered, for example via a Wafergard filter 59. Various droplet former 55 embodiments are discussed below.

The aerosol 57 is input by the droplet former 55 to a drying chamber 70. The drying chamber 70 is an elongated structure with input and output ends, a predetermined length and a predetermined horizontal dimension. The drying chamber 70 input end is connected to a source of room air via a pump 71. Air is preferably filtered, for example via a Millipore 0.22 micron Hydrophobic Millipak filter 72. The droplet former 55 is disposed at a predetermined location on the drying chamber 55. A scanning mobility particle sizer (SMPS) 33 is disposed at a predetermined location on the drying chamber 70, a predetermined distance "L" from the nebulizer 70. A vacuum pump 74 is connected to the SMPS 33. The pump 74 operates at about 1.54 liters per minute. A thermohygrometer 75, for example a DigiSense meter is disposed at the output end of the drying chamber 70, a predetermined distance "L'" further downstream from the SMPS 33.

Figure 3A:
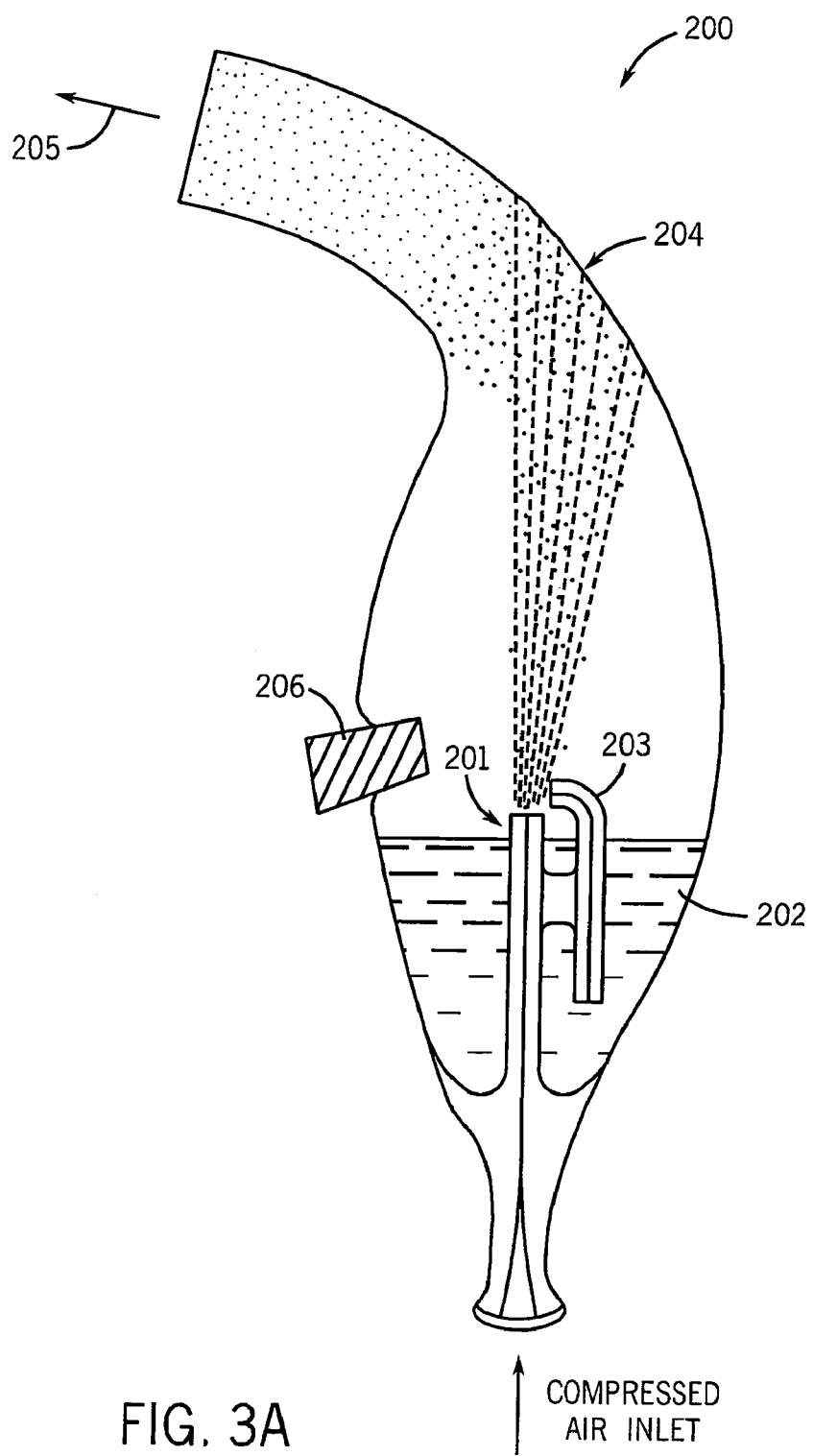

Referring to FIG. 3A, an example pneumatic nebulizer 200 which may be used to create initial droplets is disclosed. In a typical pneumatic nebulizer 200 with vent 206, compressed air exits from a small orifice 201 at high velocity creating a low pressure in the exit region. The low pressure causes liquid to be drawn into the airstream from a second tube 203 from liquid reservoir 202. The high velocity air causes the liquid to accelerate and break into droplets. The high velocity spray 204 is directed toward an impaction surface where the largest droplets are removed and an aerosol 205 is output.

Figure 3B:
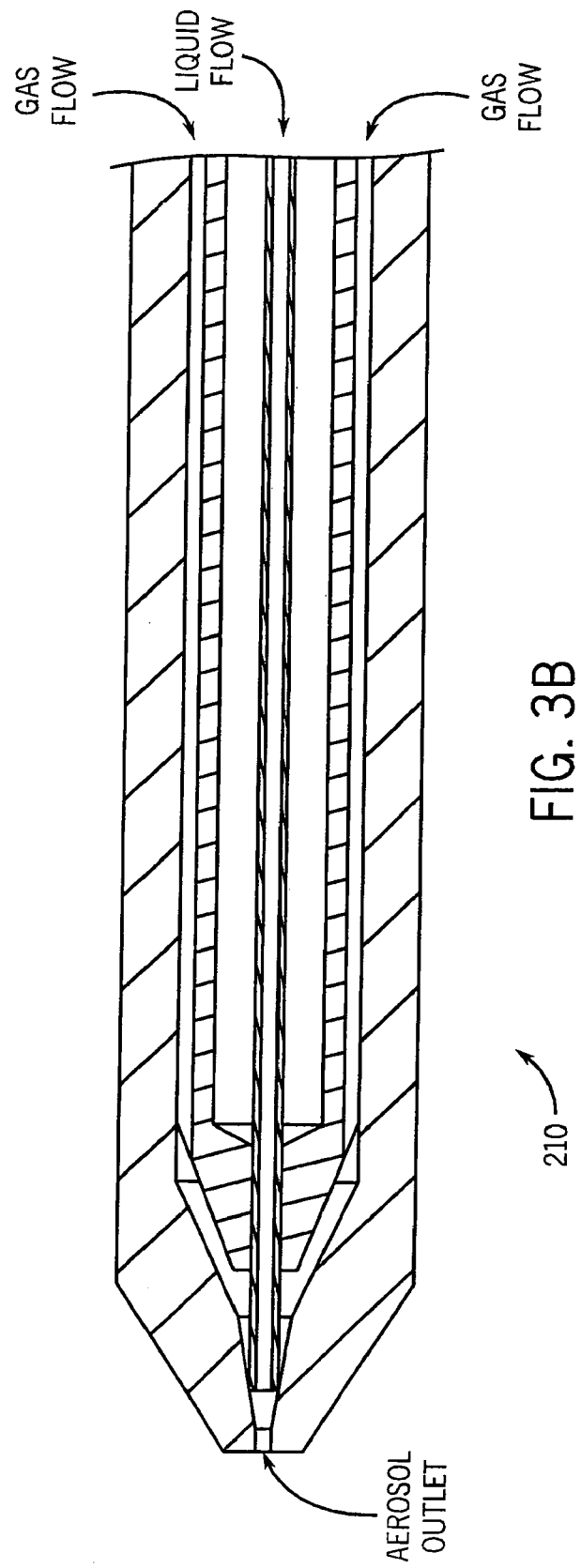

Commercially available nebulizers typically generate aerosols with droplets whose size is log-normally distributed. Median droplet sizes are typically 0.5-5.0 μm. The geometric standard deviation is typically ~2.0. The large geometric standard deviation means that the nebulizers generate a significant number of large droplets. For example, approximately 0.0003% of the droplets from a nebulizer producing an aerosol with a median droplet size of 1.0 μm and geometric standard deviation of 2.0 would be larger than 25 μm. This is an unacceptable number of large droplets for the applications described above. Examples of commercially available pneumatic nebulizers include Laskin nebulizer, Babington nebulizer, Cross-flow nebulizer, and Pre-filming nebulizer. Referring to FIGS. 3B and 3C, known concentric 210 and flow focusing pneumatic 220 nebulizers might also be used. Ultrasonic generators are also useable for generating small droplets, but less preferred than nebulizers.

As was discussed above, large droplets can be removed from the aerosol using either a plate impactor 300, shown in FIG. 4, or a virtual impactor 350 as shown in FIG. 5. In the plate impactor, the plate deflects the aerosol flow to follow an abrupt 90° bend. Droplets with sufficient inertia deviate from the flow stream, impact on the plate, and are removed from the gas stream. A virtual impactor is similar to a plate impactor except that the droplets are impacted into a quiescent region where they are withdrawn from the aerosol by a small secondary flow.

The effectiveness of impactors for removing particles is related to the Stokes number or impaction parameter. The Stokes number ($S_{tk}$) is proportional to the square of the droplet size as shown in equation 2 where $\mu_p$ is the droplet density, U is the nozzle velocity, η is the gas viscosity, and $D_j$ is the nozzle diameter.

$$S_{tk}=(\rho_p d_p^2 U)/(9\eta D_j) \quad (2)$$

Figure 6:
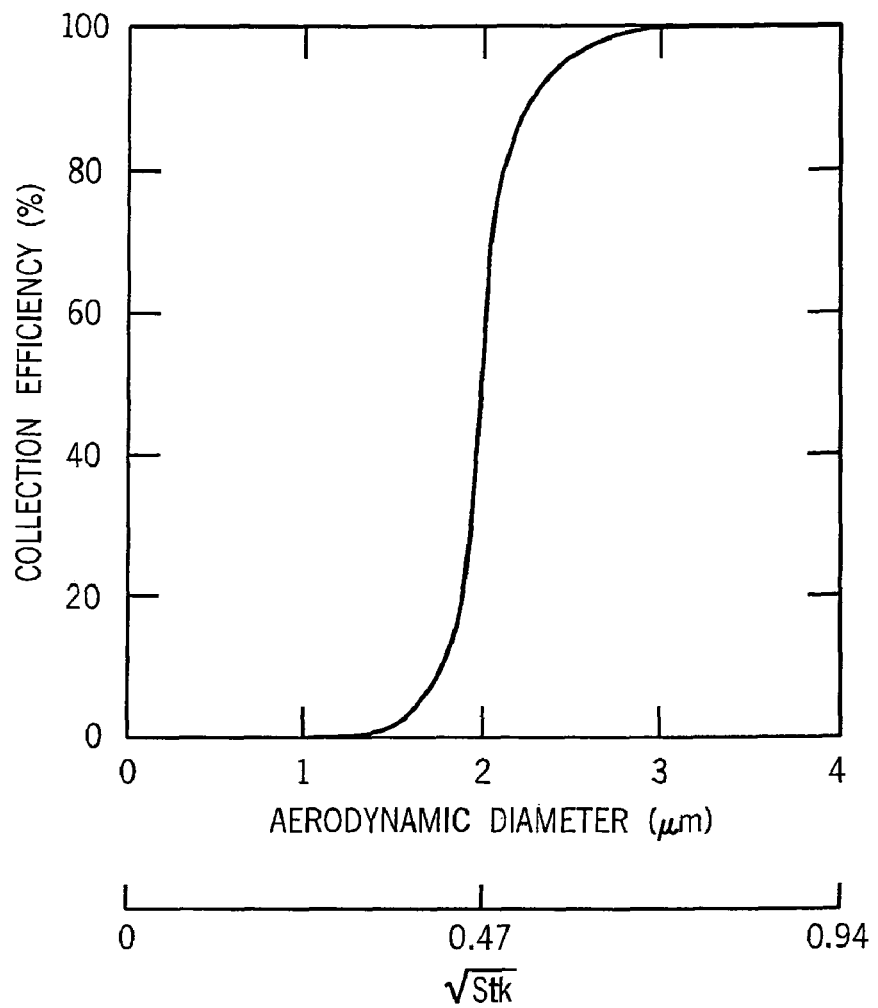
FIG. 6 is a diagram showing impactor efficiency.

Impactors can be designed with sharp efficiency curves. An impactor designed to remove 50% of the droplets >10 μm should remove virtually all droplets >25 μm. An example of a typical impactor efficiency curve is shown in FIG. 6.

Figure 7:
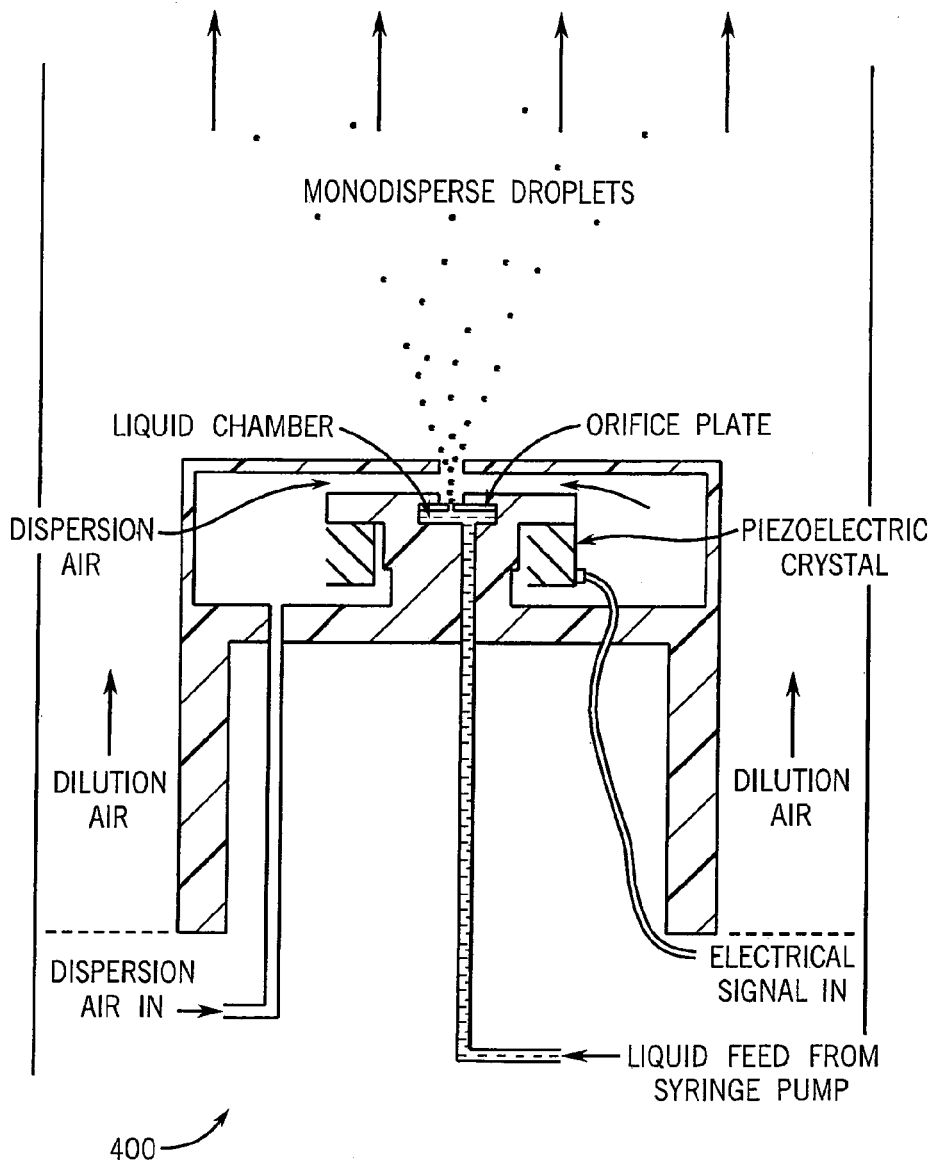
FIG. 7 illustrates an embodiment of a vibrating orifice generator used in an embodiment of the apparatus of the invention.

Another approach to generating an aerosol with small droplets is through the use of a vibrating orifice aerosol generator 400. Referring to FIG. 7, these generators 400 work by vibrating a liquid at a high frequency as it passes through a small orifice. They produce nearly monodisperse droplets. The size of the droplets generated can be calculated using equation 3 where $Q_L$ is the liquid flow rate and f is the oscillating frequency:

$$d_d=(6Q_L/\pi f)^{1/3} \quad (3)$$

A generator operating at 2 MHz with a flow rate of 0.02 ml/min would produce 10 μm droplets.

Figure 8:
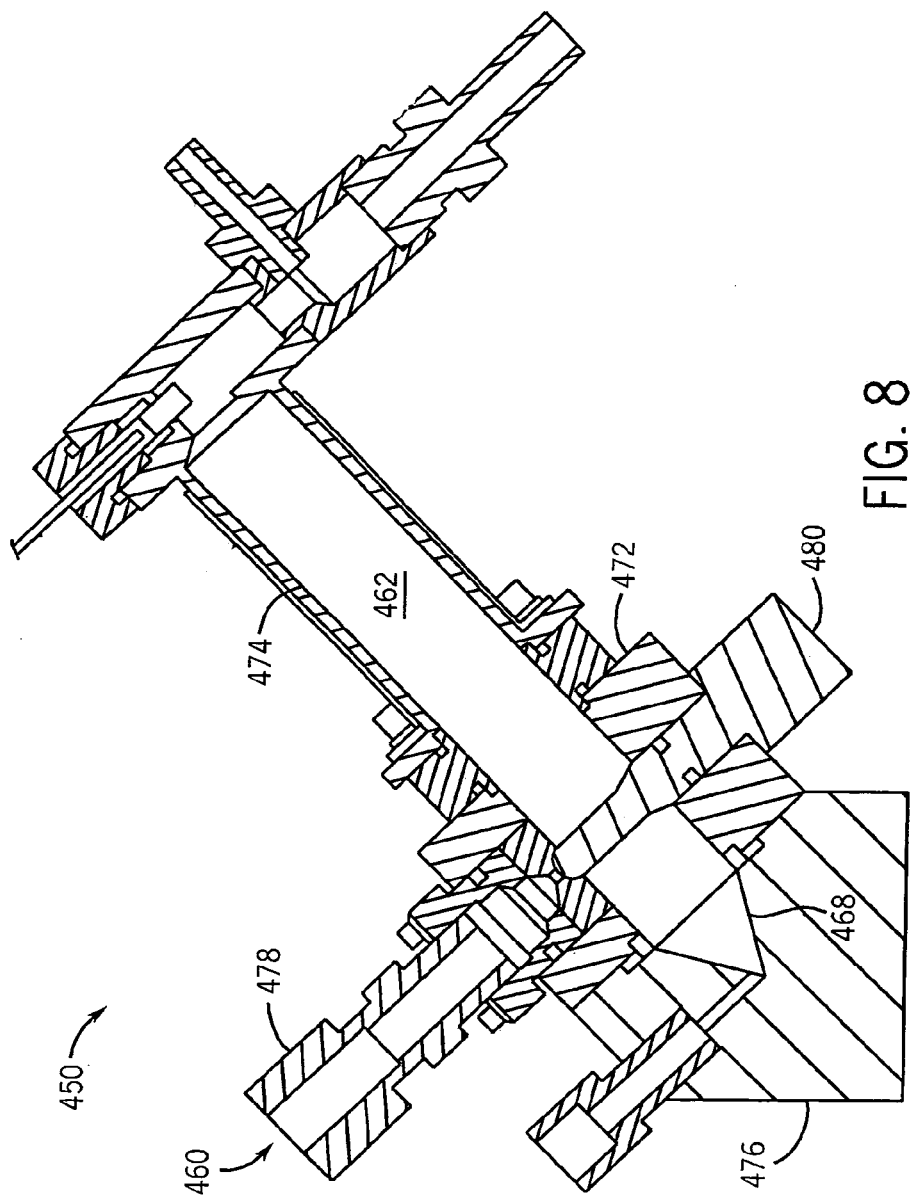
FIG. 8 is a sectional side elevational view of an embodiment of the system of the present invention including a combination nebulizer-impactor.
Figure 9:
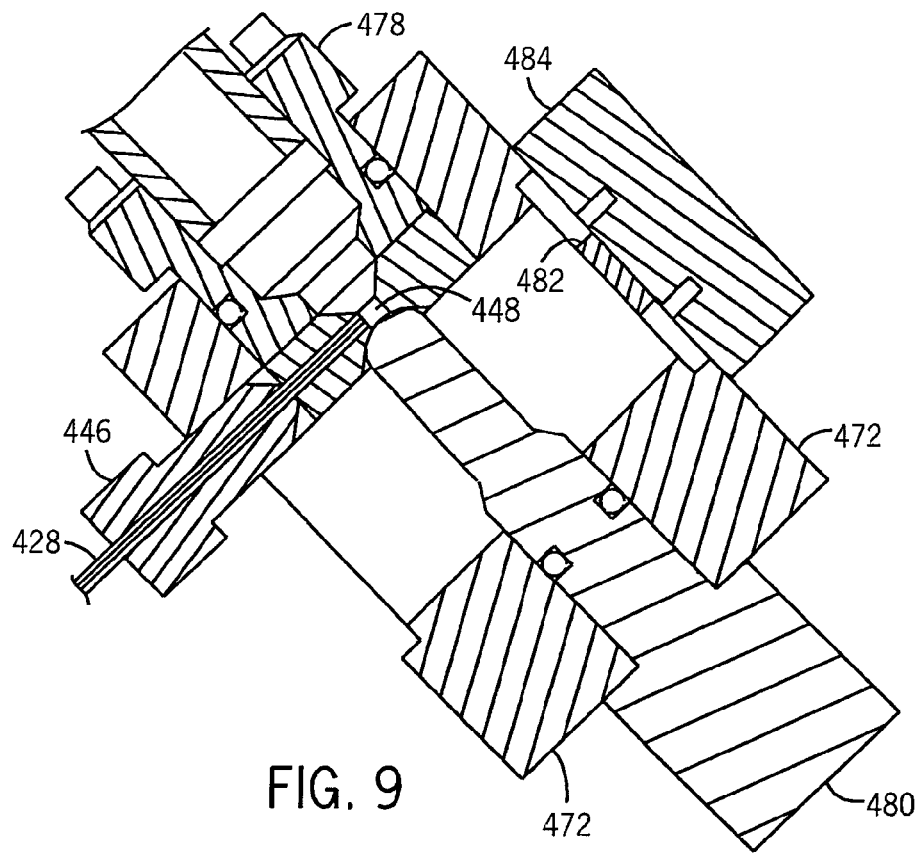
FIG. 9 is a sectional view of the combination nebulizer-impactor.
Figure 10:
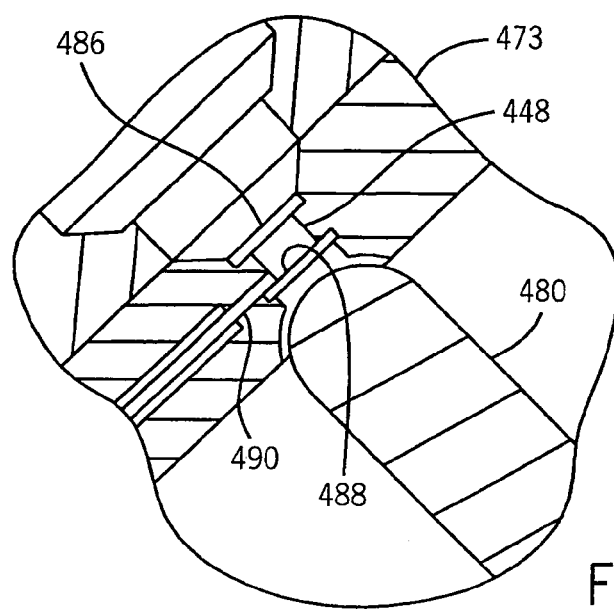
FIG. 10 is an enlarged view showing a portion of the nebulizer-impactor of FIGS. 8 and 9.

A preferred approach involves a system including a combination nebulizer-impactor 450. Referring to FIGS. 8-10, an input conduit 428 transfers fluid to a pneumatic nebulizer portion of the system. The nebulizer also receives air, nitrogen or another gas under pressure from a pressurized gas source through conduit 460. Within nebulizer 450, the liquid sample and compressed gas are merged to generate an aerosol including droplets of the liquid sample suspended in the gas.

Nebulizer 450 includes a reservoir 468 in fluid communication with the merger zone. The reservoir collects most of the liquid supplied through the input conduit 428, i.e. the liquid not used to form the aerosol droplets.

The inclined orientation shown is advantageous for liquid drainage and evacuation, although not critical. A housing of the nebulizer has several integrally coupled sections, including a stainless steel housing section 472 that encloses merger, zone 448, a steel housing section 474 forming the aerosol conditioning zone, and a housing section 476 providing the reservoir. Housing section 472 supports a fitting 478 for receiving the air or other compressed gas from conduit 460. This housing section also supports an impactor 480, through a threaded engagement that permits adjustment of the axial spacing between impactor 480 and merger zone 448.

With reference to FIG. 9, housing section 472 further supports a thermoelectric device 482 that functions to maintain a stable temperature of about 30.degree. C. in the vicinity of merger zone 448. More particularly, the thermoelectric device extracts heat from housing section 472 and transfers it to a heat sink 484. The thermoelectric device also may function as a heater for the nebulizer. The constant temperature promotes consistent droplet formation. Housing section 472 further supports bulkhead fitting 446, which secures an input conduit 428 used to transfer the sample liquid to merger zone 448.

As best seen in FIG. 10, merger zone 448 takes the form of a cylindrical chamber in a Teflon orifice housing 473. A sapphire orifice plate 486 defines an entrance or primary orifice to receive pressurized gas into the chamber from conduit 460. A sapphire orifice plate 488 defines an exit or secondary orifice through which the merged liquid and gas leave the chamber. In addition, a liquid receiving entrance 490 conducts the sample liquid into the chamber.

In one suitable version of nebulizer 450, primary orifice 486 has a diameter of 0.006 inches, and secondary orifice 488 has a diameter of 0.008 inches. The chamber has a diameter of 0.020 inches, and an axial length, i.e. space in between orifice plates 486 and 488, of 0.020 inches.

More generally, the secondary orifice diameter is larger, than the primary orifice diameter, yet less than the diameter of the cylindrical chamber. As compared to prior devices in which there is no secondary orifice and the chamber is simply open at the exit end, there is a back pressure due to the secondary orifice which increases the feed pressure to the merger zone and results in a higher kinetic energy mixing of the liquid and compressed gas. This advantageously results in smaller sample liquid droplets in the aerosol leaving the merger zone.

As the size of the secondary orifice is reduced, the droplet size is reduced and the back pressure is increased. When the sample liquid is water, it has been found satisfactory to form the secondary orifice and the primary orifice at a diameter ratio of two to one as indicated by the diameters given above. For a sample liquid with a boiling point lower than water, the preferred diameter ratio is closer to one, yet the secondary orifice remains larger than the primary orifice.

The higher energy in the merger zone more effectively breaks up the liquid. The secondary orifice also appears to improve the efficiency of the impactor downstream. The ratios of primary and secondary orifice diameters can be selected to vary the pressure at the liquid entrance to the merger zone, relative to atmospheric pressure. Depending on the diameter ratio, air inlet pressure and liquid flow rate the liquid pressure can be adjusted from below atmospheric pressure to a pressure nearly equal to the inlet air pressure.

As seen in FIG. 10, impactor 480 is disposed coaxially with merger zone 448, spaced apart in the axial direction from orifice plate 488. The impactor cooperates with housing section 472 to form a thin, somewhat hemispherical path to accommodate the flow of air and droplets beyond the merger zone. The smaller droplets tend to follow the air flow, while the larger droplets tend to collide with impactor 480 and are removed from the aerosol stream. Thus, the aerosol moving into conditioning zone 462, upwardly and to the right as viewed in FIG. 8, includes only those droplets below a size threshold determined largely by the axial spacing between secondary orifice 488 and impactor 480. The size threshold is increased by increasing the axial spacing, and reduced by moving the impactor closer to orifice plate 488.

The droplets impinging upon impactor 480 may remain on the impactor momentarily, but eventually descend to reservoir 468 then drain from the nebulizer. If desired, impactor 480 may be formed of sintered metal to provide a porous structure that more effectively prevents the larger, impacting droplets from interfering with the aerosol flow.

A secondary gas may be introduced into nebulizer 450 at a location upstream of the nebulization region. The secondary gas sweeps dead space in the nebulization region resulting in a faster response, reduced axial diffusion, and less smearing of the output due to mixing.

As was discussed above in general, once the aerosol is formed, the liquid in the droplets must be evaporated before the droplets have a chance to collide and coalesce. Drying can be accomplished using dilution air, heated air or heating the liquid.

Once the liquid is evaporated, the particles in the aerosol can be counted and/or sized by a number of techniques including, but not limited to optical particle counters (OPCs), condensation particle counters (CPCs) and scanning mobility particle Sizers (SMPS). OPCs are similar to those used in liquids. They size and count individual particles as they pass through a laser beam. Examples of OPCs include those made by Particle Measuring Systems, RION, Horiba, Particle Sizing Systems, and Hach Ultra.

Figure 11:
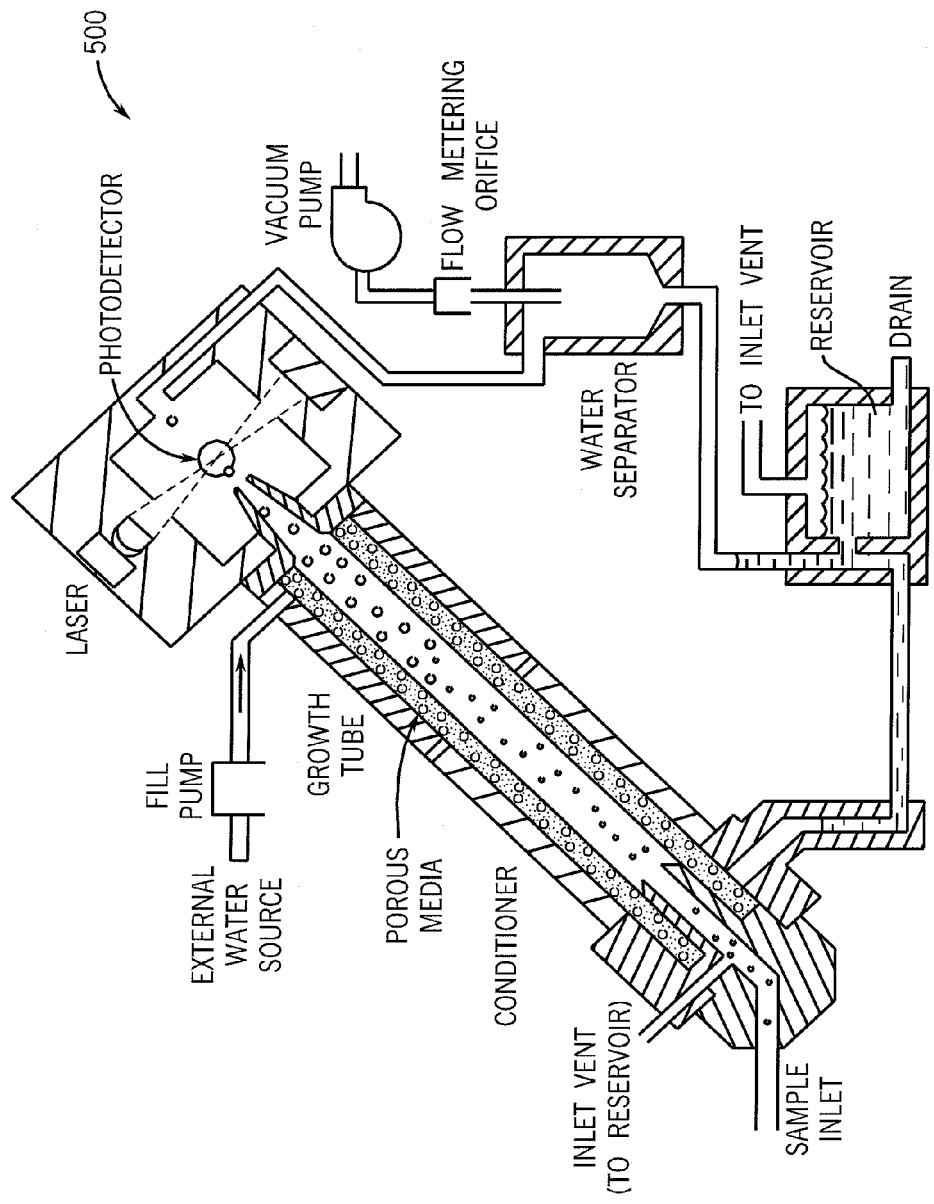
FIG. 11 illustrates an embodiment of a condensation particle counter used in an embodiment of the apparatus of the invention.

Referring to FIG. 11, a CPC 500 is capable of measuring very small particles in aerosols. They act as "particle size amplifiers" in front of a single particle counting optical detector. Particles drawn into the sensor pass through appropriately cooled and heated sections of a wet walled condenser. The differing mass and thermal diffusivities of the molecules of water vapor and air, create a supersaturated region in which the water vapor condenses on to the particles. The liquid droplets containing the particles grow to a few micrometers in diameter which are then detected optically with very high signal-to-noise. CPCs are available that use a number of working fluids including butanol and water. By varying the design conditions, they can have detection limits varying from about 1 to 20 nm. CPCs by themselves do not measure particle size distributions. They simply determine the concentration of particles larger than a size determined by their operating conditions. However, several CPCs with different detection limits can be combined to determine a size distribution. Alternately, a CPC can be combined with an SMPS to determine the size distribution.

In one embodiment, the apparatus of the present invention includes the nebulizer/impactor 450 and a CPC 500 with a detection limit preferably between 20 and 30 nm. This embodiment is believed to be best suited for high purity liquid to measure concentration above a defined threshold, but without particle size distribution (PSD) measurement.

In another embodiment, the apparatus of the invention includes a Nebulizer/Impactor 450 and a scanning mobility particle sizers (SMPS). This embodiment is believed to be best suited for determining PSD.

Although the apparatus and method of the invention has been described in connection with the field of semiconductor device manufacture, it can readily be appreciated that it is not limited solely to such field, and can be used in other fields.

Figure 12:
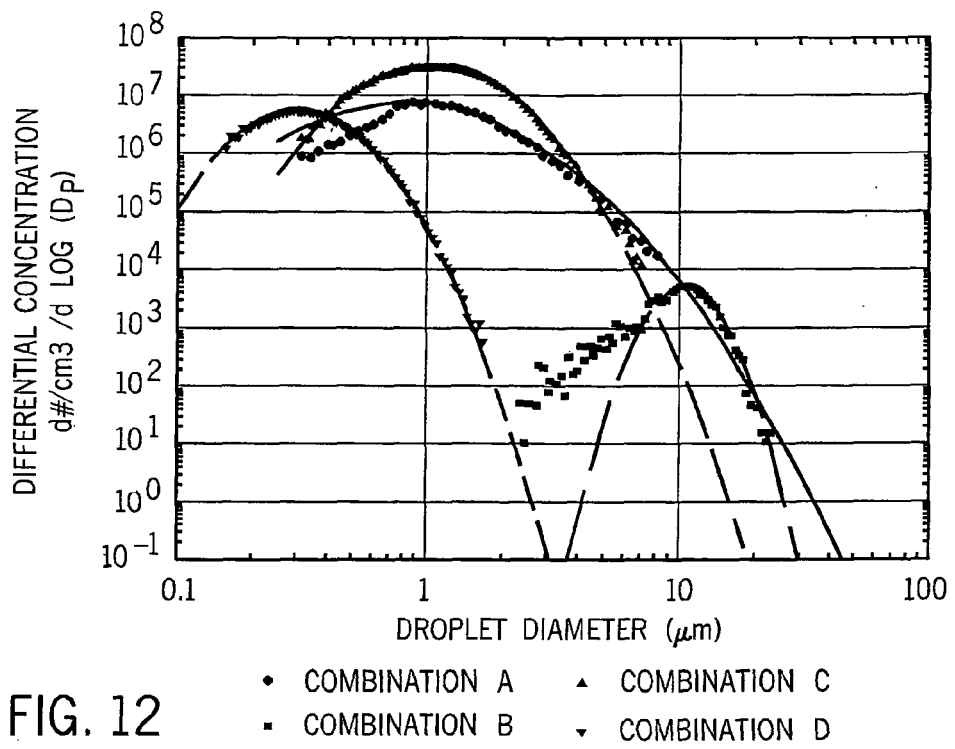
FIG. 12 is a graph of droplet size distributions produced by various combinations of nebulizers with impactors.

FIG. 12 is a graph of droplet size distributions (differential concentration vs. droplet diameter measured in um) produced by various combinations of nebulizers with impactors. Differential concentration is measured in d (#/cm$^3$) per d log ($D_P$). The graph includes lines illustrating fits of the PSD to a log-normal distribution. The droplet size distributions were measured by forming an aerosol from a sucrose solution, drying the droplets, measuring the residue PSD and calculating the droplet PSD using the equations above. The graph shows that combination D has the best distribution in that it has the smallest and most uniform droplets, and virtually no droplets are larger than 10 um.

Figure 13:
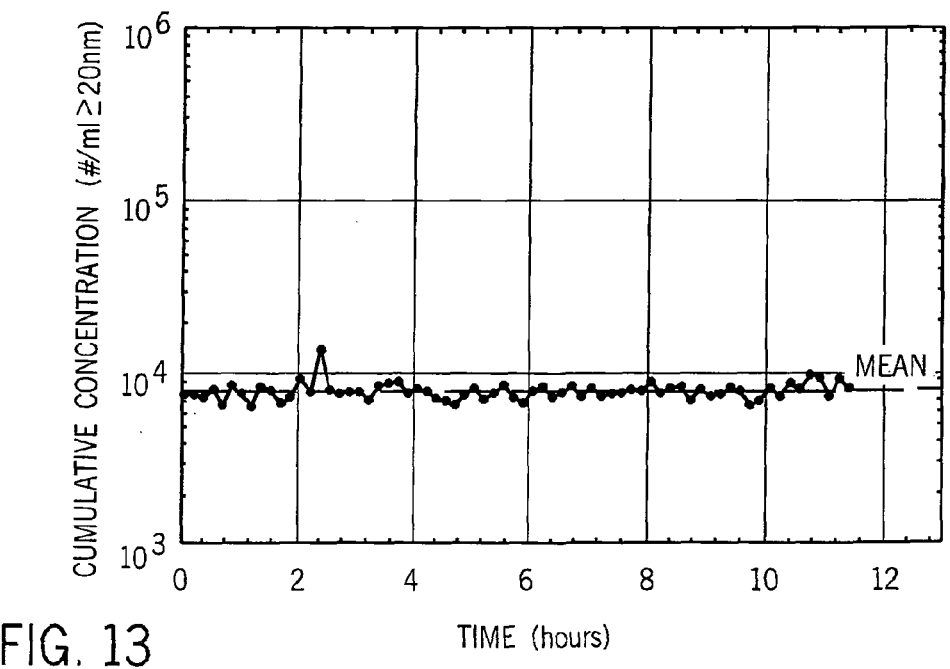
FIG. 13 is a graph of the cumulative particle concentration over time using a nebulizer-impactor combination D.
Figure 14:
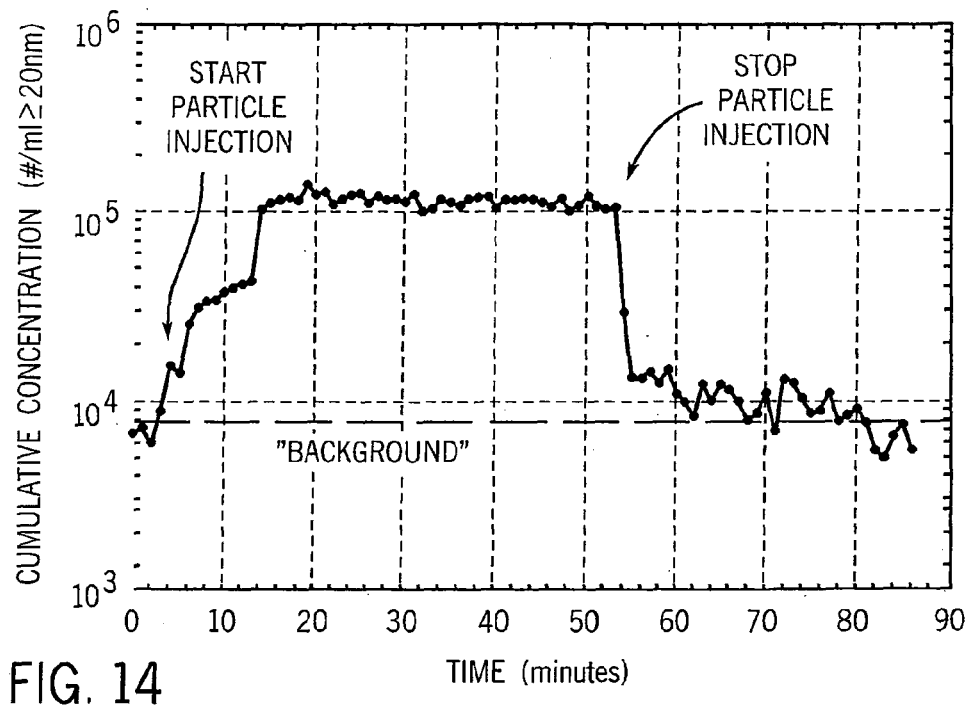
FIG. 14 is a graph of particle cumulative concentration versus time for detection of particles in ultra-pure water (UPW), with respect to 30 nm polystyrene latex (PSL) particles.
Figure 15:
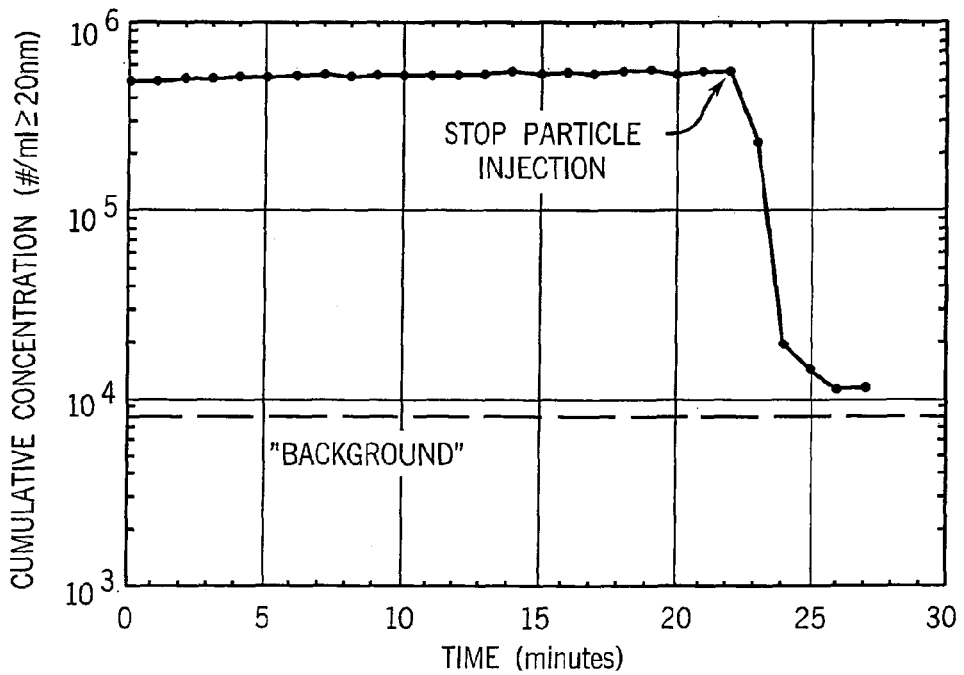
FIG. 15 is a graph of particle cumulative concentration versus time for detection of particles in ultra pure water (UPW) with respect to 22 nm silica particles.
Figure 18:
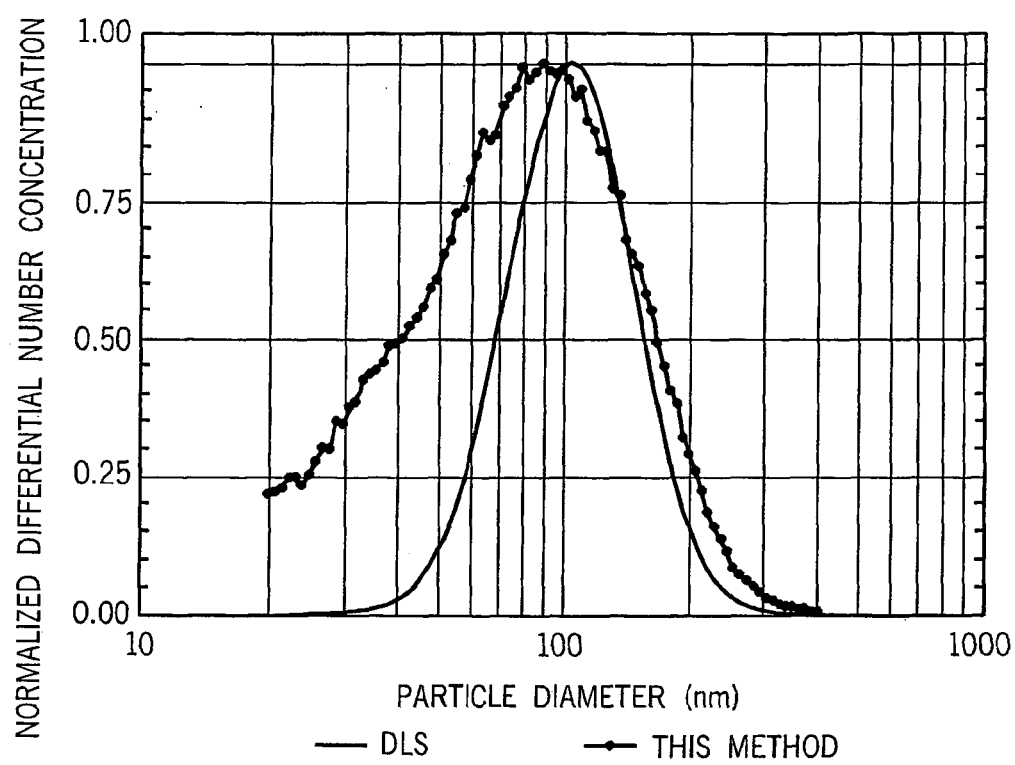
FIG. 18 compares an embodiment of the method of the invention with DLS.
Figure 19:
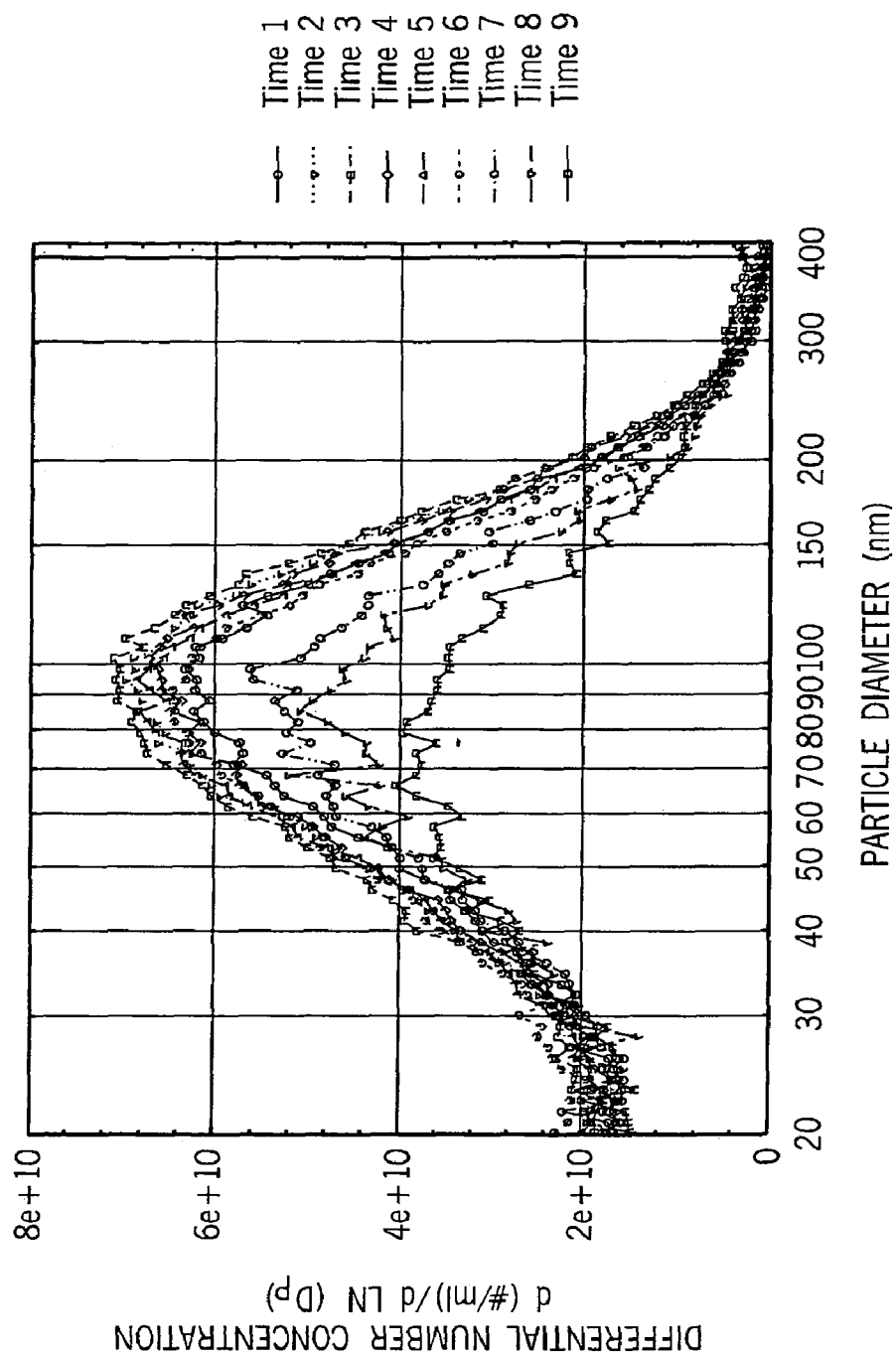
FIG. 19 shows the change in slurry PSD over time during handling via a graph of differential number concentration versus particle diameter.
Figure 20:
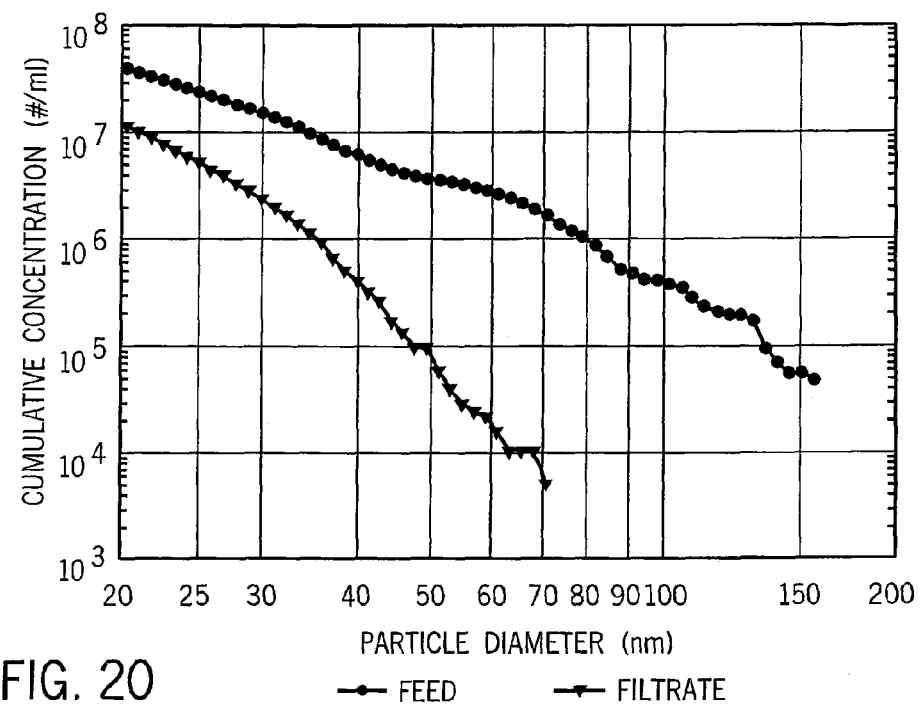
FIG. 20 shows particle concentrations of particles upstream (feed) and downstream (filtrate) of a test filter.
Figure 21:
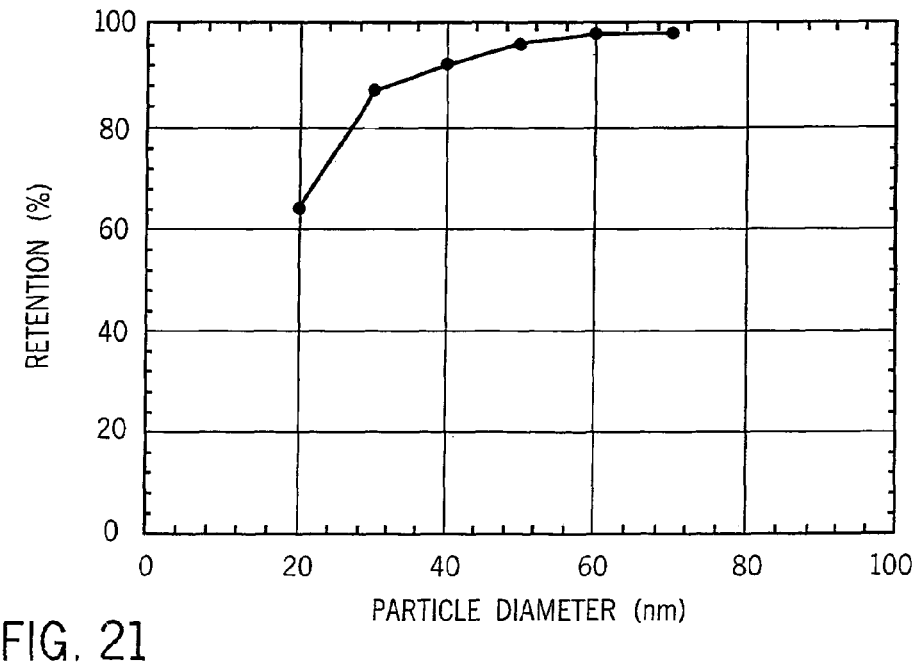
FIG. 21 is a graph of percentage retention of a filter versus particle diameter, which demonstrates retention of the filter as a function of particle size.

FIG. 13 is a graph of the cumulative particle concentration over time (in hours) measured using the nebulizer-impactor combination D. Cumulative particle concentration is measured in #/ml. greater than or equal to 20 nm. The detector is a CPC with a 20 nm detection limit. Particle detection is in ultra purified water (UPW) containing 0.4 ppb non-volatile residue (NVR). The graph shows a detection limit of approximately 8000/ml. The limit would be lower in water with lower residue content. FIGS. 14 and 15 are graphs of particle cumulative concentration versus time (in minutes) for detection of particles in ultra pure water (UPW). FIG. 15 is for 22 nm silica particles and FIG. 14 is for 30 nm polystyrene latex (PSL) particles. These graphs show the detection response of combination D (20 nm) CPC to low concentration of the two particle types. FIG. 16 is a graph of differential residual concentration (d $(nm^3/cm^3)$/d log $(D_p)$) versus particle size (in nm) which shows the ability to size 30 nm particle PSL. One sizing was conducted with a combination D apparatus with an SMPS detector. Another was conducted with a dynamic light scattering (DLS) instrument, more particularly with a NICOMP 380ZLS made by Particle Sizing Systems, Santa Barbara, Calif. The comparison shows generally good agreement. The combination D apparatus with SMPS permits measurement of actual number concentration. In contrast, DLS only provides relative concentrations. The combination D apparatus also provides a more detailed measurement of PSD. DLS on the other hand assumes that the particles are log-normally distributed. FIG. 17 is a graph of differential number concentration vs. particle diameter which measures CMP slurry PSD using a combination D apparatus with an SMPS detector. The graph shows good separation between residue and slurry particles. And FIG. 18 compares this method with DLS (using the NICOMP 380ZLS). The graph shows good agreement between the two processes. The differential number concentration determined via this method is normalized to a maximum concentration of one since DLS only gives relative concentrations. FIG. 19 shows the change in slurry PSD over time during handling via a graph of differential number concentration versus particle diameter. Successive times 1-9 are graphed. The number of smaller particle decreases over time while the number of large (i.e. greater than approximately 250 nm) increases. This indicates that particle agglomeration is occurring due to handling. This is an example of usefulness of the method of the invention. FIGS. 20 and 21 provide measurements of filter retention. Filters were challenged with polydisperse mixtures of PSL particles ranging from 20 to 500 nm in diameter. The graph (cumulative concentration in #/ml vs. particle diameter in nm) in FIG. 20 shows concentrations of particles upstream (feed) and downstream (filtrate) of the filter. The graph in FIG. 21 (percentage retention vs. particle diameter (nm)) shows retention of the filter as a function of particle size.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A method for analyzing particles in a liquid, comprising the steps of:
   a. forming an aerosol containing droplets from the liquid by;
      i. inputting the liquid to a mixing zone;
      ii. inputting pressurized gas to the mixing zone; and
      iii. restricting output from the mixing zone to generate a backpressure in opposition to input of the liquid and the pressurized gas, whereby the kinetic energy of mixing increases and decreases the size of droplets leaving the mixing zone;
   b. isolating small, less than 10 micrometers in diameter, uniformly sized droplets from the droplets;
   c. removing liquid from the small, uniformly sized droplets by evaporating to a predetermined dryness; and
   d. analyzing residual particles by counting and/or sizing.

2. The method of claim 1, wherein the median diameter of small, uniformly sized droplets is less than 1 um, and the geometric standard deviation of the small, uniformly sized droplets is smaller than or equal to 1.4.

3. The method of claim 1, wherein the method measures particle concentrations in high purity liquids defined by ASTM D 5127-07, Standard Guide for Ultra-Pure Water Used in Electronics and Semiconductor Industries, and wherein the liquid is a high purity liquid defined by ASTM D 5127-07.

4. The method of claim 1, wherein the method measures particle size distribution in colloidal suspensions and wherein the liquid and particles are in a colloidal suspension.

5. The method of claim 1, wherein the method is used to measure particle retention of a filter.

6. The method of claim 1, wherein the step of isolating small, uniformly sized droplets from the aerosol involves forming a thin, essentially hemispherical flow path of the aerosol droplets whereby large droplets of greater than 10 micrometers in diameter, leave the flow path and are impacted and removed.

7. The method of claim 1, wherein the step of removing liquid is accomplished by a process selected from the group of processes consisting of heating the aerosol, applying a stream of dilution air, applying a stream of heated air, heating the liquid, or fast evaporation.

8. The method of claim 1, wherein the step of analyzing residual particles is accomplished by a process selected from the group of processes consisting of condensation particle counting or scanning mobility particle sizing.

9. A method of analyzing particles in a liquid-, comprising the steps of:
   a. forming an aerosol containing droplets from the liquid and isolating small, less than 10 micrometers in diameter, uniformly sized droplets from the droplets by:
      i. inputting the liquid to a mixing zone;
      ii. inputting pressurized gas to the mixing zone;
      iii. restricting output from the mixing zone to generate a backpressure in opposition to input of the liquid and the pressurized gas, whereby the kinetic energy of mixing increases and decreases the size of small droplets leaving the mixing zone; and
    iv. forming a thin essentially hemispherical flow path of droplets leaving the mixing zone whereby large droplets of greater than 10 micrometers in diameter, leave the flow path and are impacted and removed;
b. removing liquid from the small, uniformly sized droplets by evaporating them to a predetermined dryness; and
c. analyzing residual particles by counting and/or sizing.

10. A method for analyzing particles in a liquid, comprising the steps of:
a. forming an aerosol containing droplets from the liquid;
b. isolating small, less than 10 micrometers in diameter, uniformly sized droplets from the droplets by forming a thin, essentially hemispherical flow path of the aerosol droplets whereby large droplets of greater than 10 micrometers in diameter, leave the flow path and are impacted and removed;
c. removing liquid from the small, uniformly sized droplets by evaporating to a predetermined dryness; and
d. analyzing residual particles by counting and/or sizing.

\* \* \* \* \*